United States Patent [19]

Mollan et al.

[11] Patent Number: 5,090,417

[45] Date of Patent: Feb. 25, 1992

[54] MEDICAL DIAGNOSTIC APPARATUS

[76] Inventors: Raymond A. B. Mollan, Orchard Hill, 167 Bangor Road, Craigavad, Hollywood, Co. Down BT18 OET; Patricia E. Boyd, 52 Wheatfield Crescent, Belfast BT14 7HT; John G. Brown, 38 Granmore Gardens, Belfast BT9 6JL, all of Ireland

[21] Appl. No.: 666,462

[22] Filed: Mar. 5, 1991

Related U.S. Application Data

[63] Continuation of Ser. No. 261,593, Oct. 24, 1988, abandoned.

[30] Foreign Application Priority Data

Oct. 22, 1987 [GB] United Kingdom ............... 8724777
Oct. 29, 1987 [GB] United Kingdom ............... 8725347

[51] Int. Cl.$^5$ .............................................. A61B 5/02
[52] U.S. Cl. ............................ 128/691; 128/693; 128/694
[58] Field of Search ........................... 128/691–694, 128/668, 713

[56] References Cited

U.S. PATENT DOCUMENTS

| | | |
|---|---|---|
| 3,847,142 | 11/1974 | Williams, Jr. et al. ............... 128/694 |
| 4,144,878 | 3/1979 | Wheeler ............... 128/693 |
| 4,169,463 | 10/1979 | Piquard ............... 128/693 |
| 4,204,545 | 5/1980 | Yamakoshi . |
| 4,206,764 | 6/1980 | Williams ............... 128/677 |
| 4,321,929 | 3/1982 | Lemelson et al. ............... 128/691 X |
| 4,367,751 | 1/1983 | Link et al. ............... 128/682 |
| 4,574,812 | 3/1986 | Arkans ............... 128/691 |

FOREIGN PATENT DOCUMENTS 8400290 2/1984 PCT Int'l Appl. .
1598984 9/1981 United Kingdom .

OTHER PUBLICATIONS

Impedance Plethysmography, A Screening Procedure to Detect Deep-Vein Thrombosis J. G. Brown, P. E. Ward (now Boyd), A. J. Wilkinson, R. A. B. Mollan From the Queen's University of Belfast and Musgrave Park Hospital Mar. 1987, pp. 264–267.

*Primary Examiner*—Lee S. Cohen
*Assistant Examiner*—John P. Lacyk
*Attorney, Agent, or Firm*—Cushman, Darby & Cushman

[57] ABSTRACT

Medical diagnostic apparatus suitable for screening use in the detection of deep veinous thrombosis in association with hip joint replacement comprises a thigh cuff (12) inflatable and deflatable to constrict and release venous blood flow in the relevant leg, a processor (10) operable automatically to control deflation of the cuff in a predetermined manner following inflation to inhibit venous flow, and a strain gauge (13) engageable around the leg below the cuff and operable to provide a signal representing venous flow caused by the controlled deflation. The deflation control is preferably effectively instantaneous by way of a solenoid valve (15) of appropriately high air flow capability.

10 Claims, 1 Drawing Sheet

MEDICAL DIAGNOSTIC APPARATUS

This is a continuation of application Ser. No. 07/261,593, filed on Oct. 24, 1988, now abandoned.

This invention concerns medical diagnostic apparatus and more particularly such apparatus for detecting deep veinous thrombosis or so-called DVT.

BACKGROUND OF THE INVENTION

DVT can be a very serious condition having a potential for fatality by causing a pulmonary embolism and it is a post-operative risk associated, although not exclusively so, with hip joint replacement surgery. It is therefore desirable that such surgery should be accompanied by application of a screening procedure to detect DVT but there is no existing procedure well suited to such use.

DVT is diagnosable by venography to a high level of accuracy and reliability. However, this conventionally involves a radiological procedure employing application of contrast media and is not best suited to the general usage which screening entails, but rather represents a good choice of confirmatory procedure to be applied in the event of a positive screening result.

Another procedure applicable to DVT diagnosis is based on ultrasound scanning, but this also is not best suited to screening use as it is complex.

Impedance plethysmography or so-called IPG is yet another procedure applicable to DVT detection but is found to require a very careful technique in practical application and is, again, inappropriate for use in screening. Development of the present invention was in fact preceded by a study of IPG to assess its potential for use in DVT screening, which study is described by J. G. Brown et al in J. Bone and Joint Surg. 69-B: 264–267, May 1987.

SUMMARY OF THE INVENTION

In any event, an object of the present invention is to provide apparatus suitable for routine use in DVT screening and, according to the invention, such apparatus comprises a tourniquet device applicable around a limb and fluid operable for inflation and deflation respectively to constrict and release venous blood flow in said limb, processor means operable automatically to control deflation of said tourniquet device in a predetermined manner following inflation to inhibit said blood flow, and an elongate strain gauge engageable around said limb distally of said tourniquet device and operable to provide a signal representative of said blood flow.

The general procedure of plethysmography of the forms at hand, be it the prior IPG form or the presently proposed strain gauge form, is that a limb is subjected to the action of a tourniquet to effect venous occlusion, blood accumulates distally of the tourniquet by continuing arterial flow until a maximum capacity is reached, and thereafter the tourniquet is released. A transducer is applied distally of the tourniquet to provide a signal output representing the blood outflow following release, which outflow can be indicative of DVT.

The general benefit of the invention in this procedure is that it does not require the same level of care as IPG to produce clinically useful results.

The processor means of the invention contributes in this last respect in that the related predetermined control of deflation avoids error which can otherwise occur as a result of variation in the manner of deflation from one operation to another. In fact deflation with the invention is preferably by way of exhaust means, such as a solenoid valve and tubing of appropriate flow capacity, operable when opened to cause effectively instantaneous deflation of the tourniquet device. Such deflation in this context is sufficiently rapid as to avoid the possibility of the consequent venous blood flow being subject to remnant pressure in the tourniquet as can occur if deflation is effected manually by a screw or other progressively operable mechanism.

The strain gauge is similarly beneficial in that it embraces the limb to operate in response to blood volume variation. This avoids the difficulties which can arise with IPG from the need to locate and engage electrodes on the limb for impedance measurement.

Preferably the processor controls the overall operation of the tourniquet device, including both inflation and deflation, to simplify further the operating procedure by users and, at the same time, avoid user-originated error.

Also the apparatus preferably entails dual tourniquet devices and transducers for respective application to a limb of direct interest and the other limb of the same kind, the output related to the latter limb being useful as a comparative reference for the output of interest.

BRIEF DESCRIPTION OF THE DRAWINGS

The foregoing and further features of the invention may be more readily understood from the following description of a preferred embodiment thereof, by way of example with reference to the accompanying drawings in which.

DESCRIPTION OF THE PREFERRED EMBODIMENT

Figure 1:
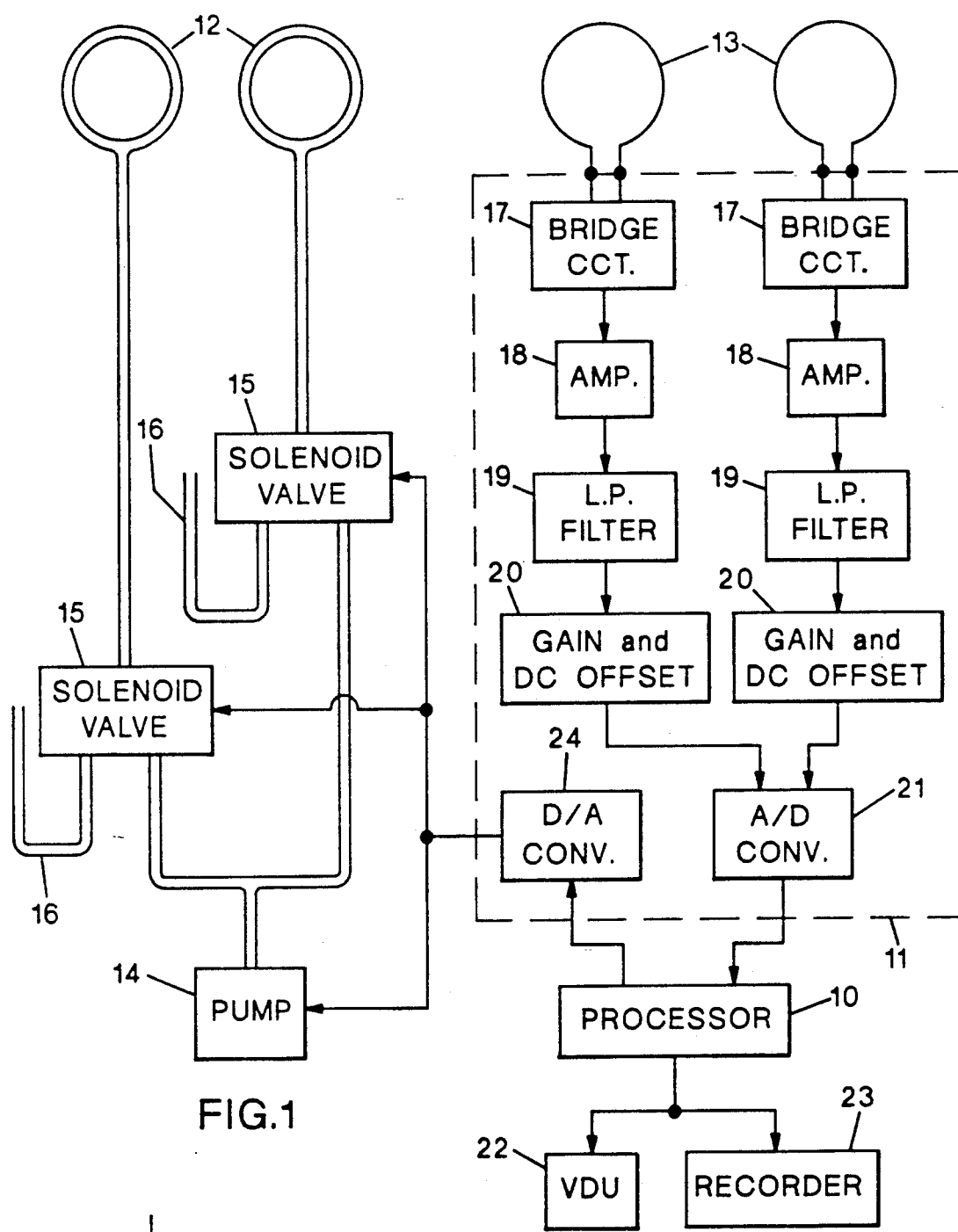
FIG. 1 schematically illustrates the relevant embodiment.

In FIG. 1 a processor 10 is connected via an interface 11 to control the operation of two tourniquet devices 12 and to receive outputs from two respective strain gauge transducers 13.

The tourniquet devices are of like thigh cuff form inflatable with air by a common pump 14, and deflated, via a respective solenoid valve 15 operated under the control of processor 10. More specifically the cuffs are inflated with the valve ON and deflated with the valve OFF, the latter condition connecting the cuffs with a vent 16 to atmosphere. The cuffs are generally conventional at a size of about 500×170 mm when deflated and have a volume of about 1 liter when inflated, but have large inlet/outlet ports allowing rapid deflation. In this last respect two ports of about 6 mm diameter per cuff have been found adequate. The valves 15 have, when OFF, flow rate capacities in the region of 500 liters/min to allow rapid deflation and the associated tubing and exhaust vent are appropriately dimensioned for the same purpose. At such flow rate capacities, a cuff inflated to one liter deflates in about 0.12 seconds. The pump has a flow rate adequate to inflate both cuffs at 4 liters/min per cuff and is subject to output pressure regulation in the region of 50 mm Hg to effect and sustain venous occlusion by way of the cuffs, the regulated pressure being adjustable.

The transducers 13 are of like elongate strain gauge form consisting of a 330 mm long Gallium-Indium filled silicone rubber tube with a stretch limiting harness.

The general opertion of the apparatus has already been described above, but it is appropriate to indicate some detail of the interface in this connection.

The transducer outputs are applied to a 2-channel balance control. Each channel includes a Wheatstone bridge circuit 17 to convert the variable resistance output of its transducer to a DC voltage, an amplifier 18 for this voltage, a 40 Hz low pass filter 19 for the amplified voltage, and a circuit 20 providing internal gain to allow calibration together with external DC offset to allow the output to be set against a baseline during data collection. This balance control is suitably mains isolated and is presently battery powered for patient safety.

The balance control outputs are applied by way of a 2-channel analogue-to-digital converter 21 to the processor from which processed outputs are applied to a visual display unit 22 and also to a recorder 23.

The interface also includes a digital-to-analogue converter 34 for applying appropriate operational signals from the processor to the pump and valves.

Figure 2:
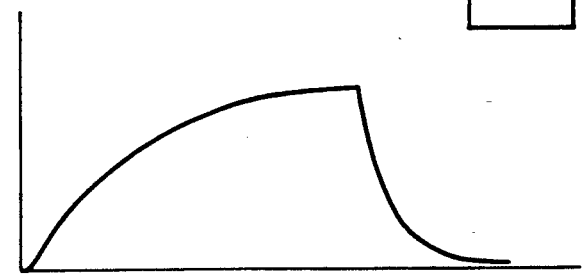
FIG. 2 graphically illustrates a typical output from the embodiment.

Processed outputs as displayed by unit 22 are typically of the form shown by FIG. 2 which graphically indicates changes in venous blood volume first as this volume increases following venous occulsion, until a maximum volume is reached, and thereafter a decrease following occlusion release. The decrease is generally exponential and rapid for a normal healthy venous system, but will be significantly slower if a DVT is present. Estimation of a given situation is suitably made by consideration of the ratio of venous outflow against venous capacitance, namely, the ratio of outflow in a given time against the maximum volume, and the processor can provide a representation of this ratio for display together with other data of interest, such as the occlusion pressure deployed.

While the present invention has been described with particular reference to the illustrated embodiment and application to the leg in association with hip joint replacement, it is of course open to variation in detail and application to the arms and for other diagnostic purposes within the scope of the appended claims.

We claim :

1. Medical diagnostic apparatus comprising:
two thigh cuffs respectively applicable around the legs of a patient;
two solenoid valves respectively connected with said cuffs and each operable in ON and OFF conditions to afford fluid communication therethrough by way of respectively different passageways;
a pump operable to provide a pressurized air supply at adjustable regulated pressure to inflate both said cuffs in unison by way of said valve ON condition passageways;
venting means for deflation of both said cuffs by way of said valve OFF condition passageways;
processor means operable automatically to control operation of said valves and pump to effect inflation of said cuffs to occlude venous blood flow in said legs, and thereafter to effect simultaneous deflation of said cuffs;
two elongate strain gauge transducers respectively engageable around said legs distally of said cuffs and operable to provide respective signals representing venous blood outflow in said legs following deflation of said cuffs. said transducers being connected with said processor means to collate said signals of the former with the times of control operations of the latter;
said venting means having a flow capacity allowing said deflation to effect substantially instantaneous release from said venous blood flow of the pressure of the preceding flow-occluding inflation.

2. Medical diagnostic apparatus comprising:
a tourniquet device applicable around a limb and fluid operable for inflation and deflation respectively to constrict and release venous blood flow in said limb;
a pump connected with said device and operable to inflate the same;
a vent connected with said device and operable to deflate the same;
a valve connected between said device on the one hand, and said pump and vent on the other hand, said valve being operable in one condition to communicate said device and pump to allow inflation of said device, and operable in another condition to communicate said device and vent to allow deflation of said device;
an elongate strain gauge transducer engageable around said limb distally of said device and operable to provide a signal representative of said blood flow; and
processor means operably connected with said pump, valve and transducer automatically to control the same in a predetermined manner to cause said pump and valve to operate to inflate said device to inhibit said blood flow, and thereafter to cause said valve to operate to deflate said device by way of said vent, while collating said transducer signal with the timing of such operations;
said vent, valve and respective communicating connections having a flow capacity allowing deflation of said device to effect substantially instantaneous release of said venous blood flow.

3. Apparatus according to any one of claim 2 wherein said tourniquet device is a thigh cuff.

4. Apparatus according to claim 2 comprising a further tourniquet device and a further elongate strain gauge transducer of like form as and applicable to the other of a pair of limbs from the first-mentioned device and transducer, said processor means being operable to control deflation of both said devices in like and simultaneous manner.

5. Apparatus according to claim 4 comprising a common pump operable under control of said processor means to effect inflation of said tourniquet devices.

6. Medical diagnostic apparatus comprising:
two thigh cuffs respectively applicable around the legs of a patient;
two solenoid valves respectively connected with said cuffs and each operable in ON and OFF conditions to afford fluid communication therethrough by way of respectively different passageways;
a pump operable to provide a pressurized air supply at adjustable regulated pressure to inflate both said cuffs in unison by way of said valve On condition passageways;
venting means dimensioned to allow substantially instantaneous deflation of both said cuffs by way of said valve OFF condition passageways;
said cuffs having about a one litre capacity and said OFF condition passageways and venting means having a flow capacity in the region of 500 litres/min. to provide for said substantial instantaneous deflation of said cuffs;

processor means operable automatically to control operation of said valves and pump to effect inflation of said cuffs to occlude venous blood flow in said legs, and thereafter to effect simultaneous deflation of said cuffs; and two elongate strain gauge transducers respectively engageable around said legs distally of said cuffs and operable to provide respective signals representing venous blood outflow in said legs following deflation of said cuffs, said transducers being connected with said processor means to collate said signals of the former with the times of control operations of the latter.

7. Medical diagnostic apparatus comprising:

a tourniquet device applicable around a limb and fluid operable for inflation and deflation respectively to constrict and release venous blood flow in said limb;

a pump connected with said device and operable to inflate the same;

a vent connected with said device and operable to deflate the same;

a valve connected between said device on the one hand, and said pump and vent on the other hand, said valve being operable in one condition to communicate said device and pump to allow inflation of said device, and operable in another condition to communicate said device and vent to allow deflation of said device;

an elongate strain gauge transducer engageable around said limb distally of said device and operable to provide a signal representative of said blood flow; and processor means operably connected with said pump, valve and transducer automatically to control the same in a predetermined manner to cause said pump and valve to operate to inflate said device to inhibit said blood flow, and thereafter to cause said valve to operate to deflate said device by way of said vent, while collating said transducer signal with the timing of such operations;

said vent, valve and respective communicating connections defining a passageway having a flow capacity in the region of 500 litres/min. for effecting substantially instantaneous deflation of said device.

8. Medical diagnostic apparatus comprising:

two thigh cuffs respectively applicable around the legs of a patient;

two solenoid valves respectively connected with said cuffs and each operable in ON and OFF conditions to afford fluid communication therethrough by way of respectively different passageways;

a pump operable to provide a pressurized air supply at adjustable regulated pressure to inflate both said cuffs in unison by way of said valve ON condition passageways;

venting means dimensioned to allow deflation of both said cuffs by way of said valve OFF condition passageways in about 0.12 seconds;

processor means operable automatically to control operation of said valves and pump to effect inflation of said cuffs to occlude venous blood flow in said legs, and thereafter to effect simultaneous deflation of said cuffs; and two elongate strain gauge transducers respectively engageable around said legs distally of said cuffs and operable to provide respective signals representing venous blood outflow in said legs following deflation of said cuffs, said transducers being connected with said processor means to collate said signals of the former with the times of control operations of the latter.

9. Medical diagnostic apparatus comprising:

a tourniquet device applicable around a limb and fluid operable for inflation and deflation respectively to constrict and release venous blood flow in said limb;

a pump connected with said device and operable to inflate the same;

a vent connected with said device and operable to deflate the same;

a valve connected between said device on the one hand, and said pump and vent on the other hand, said valve being operable in one condition to communicate said device and pump to allow inflation of said device, and operable in another condition to communicate said device and vent to allow deflation of said device;

an elongate strain gauge transducer engageable around said limb distally of said device and operable to provide a signal representative of said blood flow; and processor means operably connected with said pump, valve and transducer automatically to control the same in a predetermined manner to cause said pump and valve to operate to inflate said device to inhibit said blood flow, and thereafter to cause said valve to operate to deflate said device by way of said vent, while collating said transducer signal with the timing of such operations;

said vent, valve and respective communicating connections being dimensioned to effect deflation of said device in about 0.12 seconds.

10. Medical diagnostic apparatus comprising:

a cuff applicable around a limb of a patient;

solenoid valve means connected with said cuff and operable in ON and Off conditions to afford fluid communication therethrough by way of respectively different passageways;

pump means operable for providing a pressurized air supply to inflate said cuff by way of said valve ON condition passageway;

venting means dimensioned to allow substantially instantaneous deflation of said cuff by way of said valve OFF condition passageway;

said OFF condition passageway and venting means having a flow capacity in the region of 500 litre/min. to provide for said substantially instantaneous deflation of said cuff;

processor means operable automatically to control operation of said valve and pump to effect inflation of said cuff to occlude venous blood flow in said legs, and thereafter to effect deflation of said cuff; and elongate strain gauge transducer means engageable around said limb distally of said cuff and operable to provide respective signals representing venous blood outflow in said limb following deflation of said cuff, said transducer means being connected with said processor means to collate said signals of the former with the times of control operations of the latter.

* * * * *